(12) United States Patent
Svitek et al.

(10) Patent No.: US 12,285,555 B2
(45) Date of Patent: *Apr. 29, 2025

(54) PRIMING TRAY FOR PRIMING A FLUID SYSTEM

(71) Applicant: CardiacAssist, Inc., Pittsburgh, PA (US)

(72) Inventors: Robert G. Svitek, Freeport, PA (US); Jerry Stokes, Sarver, PA (US); Patrick A. Kelly, North Huntingdon, PA (US); Anthony McCoppin, Blawnox, PA (US); Patrick A. Murawski, Pittsburgh, PA (US); Travis Deschamps, Pittsburgh, PA (US); Patrick E. Lutz, Pittsburgh, PA (US); John C. Marous, III, Pittsburgh, PA (US)

(73) Assignee: CardiacAssist, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/369,449

(22) Filed: Sep. 18, 2023

(65) Prior Publication Data

US 2024/0009367 A1     Jan. 11, 2024

Related U.S. Application Data

(63) Continuation of application No. 16/536,069, filed on Aug. 8, 2019, now Pat. No. 11,793,918, which is a
(Continued)

(51) Int. Cl.
*A61M 1/36* (2006.01)
*A61M 60/113* (2021.01)
(Continued)

(52) U.S. Cl.
CPC ........ *A61M 1/3643* (2013.01); *A61M 1/3666* (2013.01); *A61M 60/113* (2021.01);
(Continued)

(58) Field of Classification Search
None
See application file for complete search history.

(56) References Cited

U.S. PATENT DOCUMENTS

| 4,087,864 A | 5/1978 | Labove et al. |
| 4,556,489 A * | 12/1985 | Diettrich, Jr. .......... B01D 63/14 |
| | | 210/493.5 |

(Continued)

FOREIGN PATENT DOCUMENTS

| EP | 0283850 A2 | 9/1988 |
| EP | 0378225 A2 | 7/1990 |

(Continued)

OTHER PUBLICATIONS

Extended Search Report for International Application No. 19191115.5 date of mailing Dec. 9, 2019, 7 pages.
(Continued)

*Primary Examiner* — Jonathan M Peo
(74) *Attorney, Agent, or Firm* — Seager, Tufte & Wickhem LLP

(57) ABSTRACT

A system for assisting a patient's heart has a pump, an oxygenator, a holder having a pump receiving portion for removably receiving the pump and an oxygenator receiving portion for removably receiving the oxygenator, and a harness configured to surround at least a portion of a patient's torso. The holder is connected to the harness. The system further has a brace connected to at least a portion of the harness. The brace is configured to extend behind a back portion of a user's head and to support tubing connected to at least one of the pump and the oxygenator. A priming tray and wet-to-wet connector connecting the cardiac assist system to the cannula so are also disclosed.

10 Claims, 16 Drawing Sheets

Related U.S. Application Data continuation of application No. 15/562,727, filed as application No. PCT/US2016/025264 on Mar. 31, 2016, now Pat. No. 10,695,473.

(60) Provisional application No. 62/140,778, filed on Mar. 31, 2015.

(51) Int. Cl.
*A61M 60/117* (2021.01)
*A61M 60/216* (2021.01)
*A61M 60/38* (2021.01)
*A61M 60/845* (2021.01)
*A61M 60/847* (2021.01)

(52) U.S. Cl.
CPC ........ *A61M 60/117* (2021.01); *A61M 60/216* (2021.01); *A61M 60/38* (2021.01); *A61M 60/845* (2021.01); *A61M 60/847* (2021.01); *A61M 2205/12* (2013.01); *A61M 2209/088* (2013.01)

(56) References Cited

U.S. PATENT DOCUMENTS

| | | | |
|---|---|---|---|
| 4,885,001 | A | 12/1989 | Leppert |
| 6,808,508 | B1 | 10/2004 | Zafirelis et al. |
| 8,550,973 | B2 | 10/2013 | Magovern et al. |
| 8,562,519 | B2 | 10/2013 | Smith et al. |
| 9,168,352 | B2 | 10/2015 | Kelly et al. |
| 9,446,736 | B2 | 9/2016 | Ando |
| 2003/0034030 | A1 | 2/2003 | Carlucci et al. |
| 2005/0027231 | A1 | 2/2005 | Kirchhof |
| 2009/0095783 | A1 | 4/2009 | Price |
| 2009/0099498 | A1 | 4/2009 | Demers et al. |
| 2009/0105629 | A1 | 4/2009 | Grant et al. |
| 2009/0120864 | A1 | 5/2009 | Fulkerson et al. |
| 2010/0235963 | A1 | 9/2010 | Haydon |
| 2011/0023208 | A1 | 2/2011 | Liao |
| 2011/0160649 | A1* | 6/2011 | Pan ................. A61M 1/282 177/1 |
| 2012/0143115 | A1* | 6/2012 | Muller-Spanka ... A61M 1/3627 604/4.01 |
| 2013/0284762 | A1 | 10/2013 | Voss |
| 2013/0296633 | A1 | 11/2013 | Strueber |
| 2014/0121448 | A1 | 5/2014 | Smith et al. |
| 2014/0234166 | A1 | 8/2014 | Erickson |
| 2014/0263018 | A1 | 9/2014 | Fuhriman |
| 2015/0367062 | A1 | 12/2015 | Brugger et al. |

FOREIGN PATENT DOCUMENTS

| | | |
|---|---|---|
| EP | 02082757 A2 | 7/2009 |
| JP | 62690 Y2 | 1/1987 |
| JP | 2002536126 A | 10/2002 |
| JP | 2008284031 A | 11/2008 |
| JP | 2009172063 A | 8/2009 |
| JP | 6287645 B2 | 3/2018 |
| JP | 2018513732 A | 5/2018 |
| WO | 0047248 A1 | 8/2000 |
| WO | 2004064896 A2 | 8/2004 |
| WO | 2016161114 A1 | 10/2016 |

OTHER PUBLICATIONS

International Search Report and Written Opinion for International Application No. PCT/US16/25264, date of mailing Jun. 20, 2016, 7 pages.

* cited by examiner

PRIMING TRAY FOR PRIMING A FLUID SYSTEM

CROSS-REFERENCE TO RELATED APPLICATIONS

This application is a continuation application of U.S. application Ser. No. 16/536,069, filed Aug. 8, 2019, now U.S. Pat. No. 11,793,918, which is a continuation application of U.S. application Ser. No. 15/562,727, filed Sep. 28, 2017, now U.S. Pat. No. 10,695,473, which is a United States national phase application of International Application No. PCT/US2016/025264, filed Mar. 31, 2016, which claims priority to U.S. Provisional Application No. 62/140,778, filed Mar. 31, 2015, the disclosures of which are incorporated by reference herein in its entirety.

BACKGROUND OF THE INVENTION

Field of the Invention

The disclosure relates to a system for assisting a patient's heart including a pump and oxygenator for introducing oxygenated blood to the pulmonary artery of a patient and, in particular, to a holder and harness for mounting the system to the patient.

Description of Related Art

Current therapy for circulatory support for oxygen infusion into a patient's blood may involve a number of adverse events that limit the therapy's application. These adverse situations include infection, inflammation, fluid build-up in the lungs, the possibilities of stroke and internal bleeding, and device/vein blockage that reduces flow in the support system and thus severely affects patients. The interface of blood with artificial materials can cause thrombus (clotting), which is managed by anti-coagulation, which can give rise to internal bleeding. If anti-coagulation is insufficient, clots that develop in the artificial devices can release and flow into the body and generate strokes. The contact of blood with artificial materials can cause inflammation and infection, even though the materials used are tested to be biocompatible.

Historically, left and/or right ventricular assist devices (LVAD and/or RVAD) have been used for patients requiring surgical intervention without a percutaneous or cath lab option available. These surgical LVADs and/or RVADs have been used for patients with myocardial infarction, acute ischemic events (with large left and right propagation), cardiogenic shock, LVAD created right ventricular (RV) dysfunction, post-transplant RV failure, and pulmonary hypertension. Acute myocardial infarction and cardiogenic shock have been treated with intraaortic balloon pumps (IABPs) and maximal inotropic support, to which many patients become refractory. Surgically implanted LVADs can create a significant septal shift that leads to a dynamic change in the Starling curve that abruptly places patients into severe RV failure. Patients bridged to transplant from an LVAD with severe RV failure, can be limited in post-transplant survival. Secondary pulmonary hypertension leads to an exacerbation of RV failure in acute and chronic situations, which are commonly treated with LVADs.

The current TandemHeart PTVA cardiac assist system manufactured by CardiacAssist, Inc. is a percutaneous left ventricular assist system having a centrifugal pump, a 21 Fr, approximately 65 cm long uptake cannula designed to be placed across the interatrial septum using a standard transseptal puncture technique, and a 15 or 17 Fr return cannula; with the cannulae connected to the pump using standard ⅜-inch surgical tubing. Systemic flow rates of 3.5-4.0 Liters/Min can be achieved. The TandemHeart device has been studied on acute cardiogenic shock patients and was found to confer a significant hemodynamic benefit compared to IABPs. It is approved by the FDA for temporary (<6 hr) left ventricular mechanical circulatory support. The TandemHeart system can also be used in connection with an oxygenator for providing extracorporeal membrane oxygenation, often referred to as ECMO, which can be done in venoarterial configuration to support cardiac and respiratory function or veno-venous configuration to support just respiratory function. The TandemHeart system can also be used with cardiac assist systems that pump oxygenated blood received from the left atrium through a transseptal cannula and return the blood to the arterial system as disclosed, for example, in U.S. Pat. No. 6,808,508 to Zafirelis, et al., which is incorporated by reference herein in its entirety.

At present, the cardiac assist system can be attached to a patient by a belt or strap. Elements of the cardiac assist system can also be held by being mounted to stationary objects, such as IV poles, stands, and the like. However, improved mounting systems that increase patient mobility and reduce the length of connecting tubing are desirable.

SUMMARY OF THE INVENTION

In view of the foregoing, it is therefore of great clinical value to develop systems that reduce the adverse situations noted above. It is desirable to develop a system with a minimal amount of artificial material, that enables a smoothest path of flow so as to minimize blood flow disturbance, and allows the patient to be mobile, potentially even walking, all while flowing a high quantity of blood so as to provide complete oxygen source and thus allow flexibility of the treating physicians to avoid other alternate sources of oxygen, such as mechanical ventilators, which are known to cause lung fiber damage. There is also a need for improved systems for assisting a patient's heart including a pump and oxygenator for introducing oxygenated blood to the pulmonary artery of a patient and, in particular, to a holder and harness for mounting the system to the patient. There is an additional need for a fast-priming mechanism for priming a pump and/or oxygenator very quickly to reduce the patient degradation during extended set up time for typical systems. There is a further need for a connector that can be quickly and easily connected and disconnected, as typical systems are not easily connected and disconnected and thus are more difficult to prime and to change components when complications occur. Systems configured to address these issues are discussed herein.

According to one aspect of the disclosure, a system for assisting a patient's heart may include a pump; an oxygenator; a holder having a pump receiving portion for removably receiving the pump and an oxygenator receiving portion for removably receiving the oxygenator; a harness configured to surround at least a portion of a patient's torso, with the holder being connected to the harness; and a brace connected to at least a portion of the harness. The brace may be configured to extend behind a back portion of a user's head and to support tubing connected to at least one of the pump and the oxygenator.

According to other aspects of the present disclosure, the brace may have an attachment portion for connecting the brace to the harness. The attachment portion may be removably connected to the harness by one or more fastening elements. The brace may have a support portion extending from the attachment portion for supporting the tubing. The brace has one or more tubing clips for securing the tubing. The holder may have at least one connection member for releasably connecting the pump and the oxygenator to the holder. The pump receiving portion may have a flat surface shaped to engage a base of the pump and one or more tabs for releasably engaging an outer surface of the pump. The oxygenator receiving portion may be shaped to receive a cylindrically-shaped oxygenator. The holder may have a first attachment member and the harness has a second attachment member for removably connecting the holder to the harness. The harness may have one or more sections that are adjustable in size to conform to a patient's body. The harness may have a central opening for placing the harness over a user's head. The harness may have a connection member for securing the harness to a patient's body. The connection member may be a hook and loop fastener. The tubing may have an inlet tube connected to an inlet of the pump, an outlet tube connected to an outlet tube, and a connection tube connected between an outlet of the pump and an inlet of the oxygenator. At least one of the inlet tube, the outlet tube, and the connection tube may be connected to the brace by one or more tubing clips.

According to other aspects of the present disclosure, a system for assisting a patient's heart may include a pump; an oxygenator; a tubing having an inlet tube connected to an inlet of the pump, an outlet tube connected to an outlet tube, and a connection tube connected between an outlet of the pump and an inlet of the oxygenator; a holder having a pump receiving portion for removably receiving the pump and an oxygenator receiving portion for removably receiving the oxygenator; a harness configured to surround at least a portion of a patient's torso, the holder being connected to the harness; and a brace connected to at least a portion of the harness, the brace configured to extend behind a back portion of a user's head and to support tubing connected to at least one of the pump and the oxygenator, wherein the brace has an attachment portion for connecting the brace to the harness and a support portion extending from the attachment portion for supporting the tubing. The pump receiving portion has a flat surface shaped to engage a base of the pump and one or more tabs for releasably engaging an outer surface of the pump. The oxygenator receiving portion is shaped to receive a cylindrically-shaped oxygenator. The holder has a first attachment member and the harness has a second attachment member for removably connecting the holder to the harness According to other aspects of the present disclosure, a patient harness for supporting a system for assisting a patient's heart may include a holder having a pump receiving portion configured for removably receiving a pump and an oxygenator receiving portion configured for removably receiving an oxygenator; a harness configured to surround at least a portion of a patient's torso, the holder being connected to the harness; and a brace connected to at least a portion of the harness, the brace configured to extend behind a back portion of a user's head and to support tubing connected to at least one of the pump and the oxygenator, wherein the brace has an attachment portion for connecting the brace to the harness and a support portion extending from the attachment portion for supporting the tubing.

According to another aspect of the disclosure, a priming tray for priming a pump and/or oxygenator of a cardiac assist system includes a container defining an interior reservoir. The container includes an inlet port and an outlet port. Each port is covered by a self-sealing valve connector that permits an open end of connecting tubing to be inserted therethrough and which automatically reseals when the end of the connecting tubing is removed from the valve connector.

According to another aspect of the disclosure, a connector for priming and establishing a fluid connection between connecting tubing and a cannula is provided. The connector includes a housing having a first port in fluid connection with a cannula and a second port configured to be removably connected to the connecting tubing. The housing can further include a port for introducing fluid to the interior of the housing and/or for permitting trapped air to escape from the interior of the housing. The port can be covered by a hydrophobic filter, a one-way valve, or a ball valve. The port can also be covered by a piercable septum for allowing a syringe to be connected thereto for expelling fluid to the housing or for drawing trapped air from the interior of the housing.

Various other aspects of the disclosure are further described in one or more of the following clauses:

Clause 1: A system for assisting a patient's heart, the system comprising:
 a pump;
 an oxygenator;
 a holder having a pump receiving portion for removably receiving the pump and an oxygenator receiving portion for removably receiving the oxygenator;
 a harness configured to surround at least a portion of a patient's torso, the holder being connected to the harness; and
 a brace connected to at least a portion of the harness, the brace configured to extend behind a back portion of a user's head and to support tubing connected to at least one of the pump and the oxygenator.

Clause 2: The system of clause 1, wherein the brace has an attachment portion for connecting the brace to the harness.

Clause 3: The system of clause 2, wherein the attachment portion is removably connected to the harness by one or more fastening elements.

Clause 4: The system of any of clauses 1-3, wherein the brace has a support portion extending from the attachment portion for supporting the tubing.

Clause 5: The system of any of clauses 1-4, wherein the brace has one or more tubing clips for securing the tubing.

Clause 6: The system of any of clauses 1-5, wherein the holder has at least one connection member for releasably connecting the pump and the oxygenator to the holder.

Clause 7: The system of any of clauses 1-6, wherein the pump receiving portion has a flat surface shaped to engage a base of the pump and one or more tabs for releasably engaging an outer surface of the pump.

Clause 8: The system of any of clauses 1-7, wherein the oxygenator receiving portion is shaped to receive a cylindrically-shaped oxygenator.

Clause 9: The system of any of clauses 1-8, wherein the holder has a first attachment member and the harness has a second attachment member for removably connecting the holder to the harness.

Clause 10: The system of any of clauses 1-9, wherein the harness has one or more sections that are adjustable in size to conform to a patient's body.

Clause 11: The system of any of clauses 1-10, wherein the harness has a central opening for placing the harness over a user's head.

Clause 12: The system of any of clauses 1-11, wherein the harness has a connection member for securing the harness to a patient's body.

Clause 13: The system of clause 12, wherein the connection member is a hook and loop fastener.

Clause 14: The system of any of clauses 1-13, wherein the tubing has an inlet tube connected to an inlet of the pump, an outlet tube connected to an outlet tube, and a connection tube connected between an outlet of the pump and an inlet of the oxygenator.

Clause 15: The system of clause 14, wherein at least one of the inlet tube, the outlet tube, and the connection tube are connected to the brace by one or more tubing clips.

Clause 16: A system for assisting a patient's heart, the system comprising:
a pump;
an oxygenator;
a tubing having an inlet tube connected to an inlet of the pump, an outlet tube connected to an outlet tube, and a connection tube connected between an outlet of the pump and an inlet of the oxygenator;
a holder having a pump receiving portion for removably receiving the pump and an oxygenator receiving portion for removably receiving the oxygenator;
a harness configured to surround at least a portion of a patient's torso, the holder being connected to the harness; and
a brace connected to at least a portion of the harness, the brace configured to extend behind a back portion of a user's head and to support tubing connected to at least one of the pump and the oxygenator,
wherein the brace has an attachment portion for connecting the brace to the harness and a support portion extending from the attachment portion for supporting the tubing.

Clause 17: The system of clause 16, wherein the pump receiving portion has a first surface shaped to engage a base of the pump and one or more tabs for releasably engaging an outer surface of the pump.

Clause 18: The system of clause 16 or clause 17, wherein the oxygenator receiving portion is shaped to receive a cylindrically-shaped oxygenator.

Clause 19: The system of any of clauses 16-18, wherein the holder has a first attachment member and the harness has a second attachment member for removably connecting the holder to the harness.

Clause 20: A patient harness for supporting a system for assisting a patient's heart, the harness comprising:
a holder having a pump receiving portion configured for removably receiving a pump and an oxygenator receiving portion configured for removably receiving an oxygenator;
a harness configured to surround at least a portion of a patient's torso, the holder being connected to the harness; and
a brace connected to at least a portion of the harness, the brace configured to extend behind a back portion of a user's head and to support tubing connected to at least one of the pump and the oxygenator,
wherein the brace has an attachment portion for connecting the brace to the harness and a support portion extending from the attachment portion for supporting the tubing.

BRIEF DESCRIPTION OF THE DRAWINGS

Some of the advantages and features of the preferred aspects or embodiments have been summarized hereinabove. These aspects or embodiments, along with other potential aspects or embodiments will become apparent to those skilled in the art when referencing the following drawings in conjunction with the detailed descriptions as they relate to the figures.

DESCRIPTION OF THE INVENTION

Figure 1:
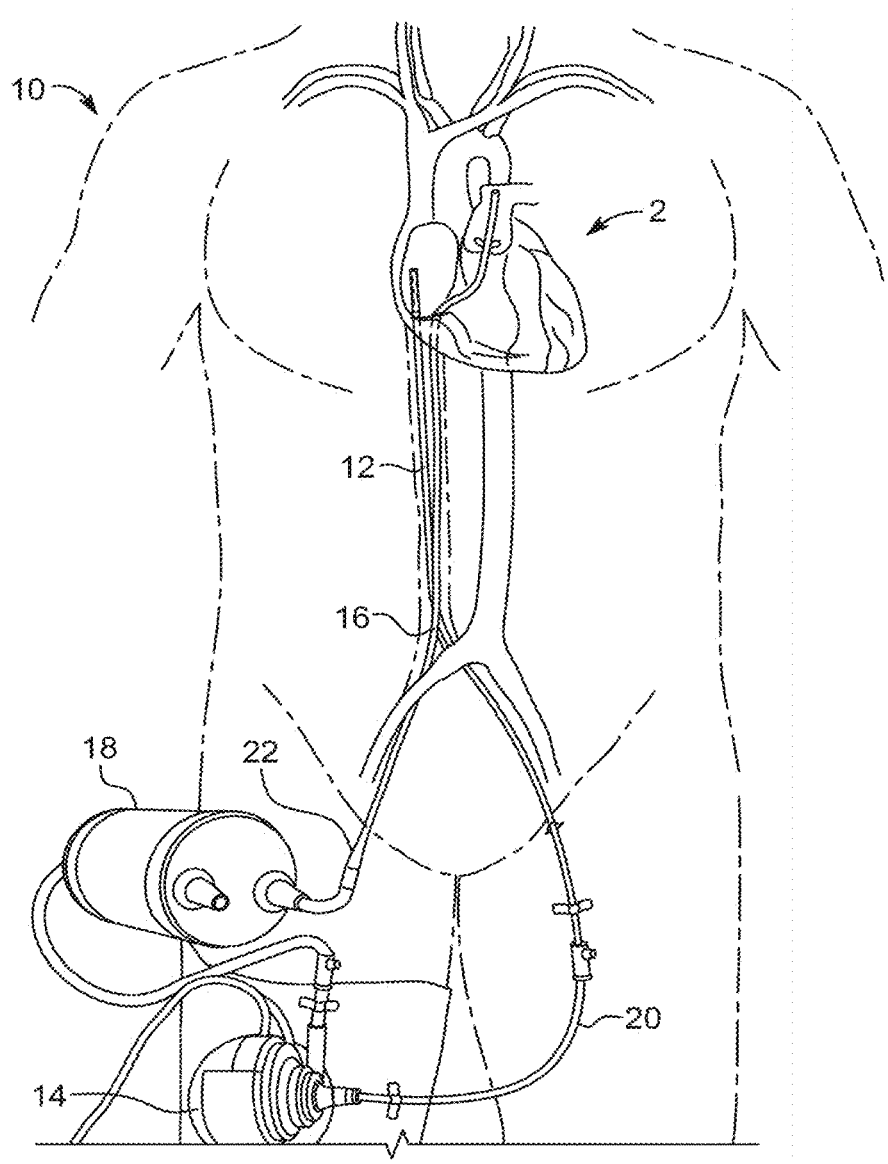
FIG. 1 is a schematic drawing of a cardiac assist system according to an aspect of the disclosure.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures. When used in relation to a blood pump, oxygenator, cannula, connector, and any other component of a cardiac assist system, the term "distal" refers to a portion of a blood pump, oxygenator, cannula, and/or connector, nearest to a patient, such as an intended access site on the patient's body, when a blood pump, oxygenator, cannula, and/or connector, is oriented for connecting to a patient. The term "proximal" refers to a portion of a blood pump, oxygenator, cannula, and/or connector farthest away from a patient, such as an intended access site on the patient's body, when a blood pump, oxygenator, cannula, and/or connector is oriented for connecting to a patient. The term "radial" refers to a direction in a cross-sectional plane normal to a longitudinal axis of a blood pump, oxygenator, cannula, and/or connector extending between proximal and distal ends. The term "circumferential" refers to a direction around an inner or outer surface of a blood pump, oxygenator, cannula, and/or connector. The term "axial" refers to a direction along a longitudinal axis of a blood pump, oxygenator, cannula, and/or connector extending between the proximal and distal ends. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

Cardiac Assist System

With reference to FIG. 1, a system 10 for cardiac assistance of a patient's heart 2, such as for bypassing the left and/or right ventricle to provide oxygenated blood to the arterial system via the femoral, axillary, or the pulmonary artery, is illustrated. A cardiac assist system, which can be adapted for use with the holders, harnesses, connectors, and priming apparatus of the present disclosure, is generally disclosed in U.S. Pat. No. 8,550,973 to Magovern et al., which is incorporated by reference in its entirety. Another right heart assist system and a method of applying the system to a patient are disclosed in U.S. Pat. No. 8,562,519 to Smith et al., which is also incorporated by reference herein. Another cardiac assist system is disclosed in U.S. Pat. No. 6,808,508 to Zafirelis, et al., which is discussed hereinabove and also incorporated by reference herein.

The system 10, as shown in FIG. 1, includes a drainage cannula 12 that is adapted to extend from the right atrium of the heart in fluid communication with a pump 14 to provide blood to the pump 14. The system 10 also includes a femoral or pulmonary artery cannula 16. In some aspects, the cannula 16 can be at least 17 cm in length when configured for insertion into the femoral artery and at least 70 cm in length when configured for insertion into the pulmonary artery, and adapted to extend from the patient's groin to the pulmonary artery of the patient to provide blood to the pulmonary artery for right ventricular support. The cannula 16 can be a dual lumen cannula in the internal jugular vein, a surgical cannula connected directly to the heart, and, as will be discussed herein, can be connected with or without an oxygenator. The cannula 16 can be a steerable cannula with a steerable mechanism to control the position and shape of the cannula body. Further, the cannula 16 can have a balloon tip to enable self-direction and placement into a flow-directed vessel. An additional lumen can enable placement of additional wires or clot removal devices into the pulmonary artery or vessel. Further, if the cannula 16 is a dual lumen cannula, the transition taper between the side holes on the cannula body can have cut-outs to enable strain relief during placement or manipulation or curving of the cannula around a tortuous anatomy. Finally, a coating on the tip of the cannula 16 can enable radiopacity for placement and position determination. In some aspects, the cannula 16 can be the cannula described in U.S. Pat. No. 9,168,352 to Kelly et al.

The pulmonary artery cannula 16 is in fluid communication with the pump 14, whereby the heart's right ventricle is essentially bypassed by draining the right atrium and pumping blood into the pulmonary artery thereby allowing the right ventricle of the patient to rest and enable right ventricular support. Preferably, the pump 14 is a ventricular assist pump, such as a centrifugal, axial, mixed, or roller pump, as is known in the art, that produces adequate flow rates through the system to achieve desired therapeutic results (e.g., either cardiac assist or right ventricular bypass). A suitable pump 14 for use with the above-described system 10 is disclosed in U.S. Pat. No. 6,808,508 to Zafirelis et al.

The system 10 can also include an oxygenator 18 in fluid communication with the pump 14. The oxygenator 18 receives blood pumped by the pump 14, oxygenates the blood, and through the pulmonary artery cannula 16, provides oxygenated blood to the pulmonary artery. The oxygenator 18 can be a spiral wound sheet membrane type oxygenator or any of the hollow fiber membrane type oxygenators including, but not limited to, the CAPIOX® oxygenator manufactured by the Terumo Cardiovascular Group, MINIMAX* or AFINITY® oxygenator manufactured by Medtronic, QUADROX® oxygenator manufactured by Maquet, Gish Vision oxygenator manufactured by Gish Biomedical, Cobe Optima oxygenator, and others. A controller that may be used for the pump and oxygenator is described in U.S. Pat. No. 6,808,508 to Zafirelis et al.

In some aspects, the system 10 can be applied to a patient according to the following method. The method includes inserting a tip of the pulmonary artery cannula 16 into a right femoral vein of a patient, and moving the tip through the right femoral vein until side holes of the cannula 16 in proximity to the tip are disposed in the pulmonary artery. Then, the drainage cannula 12 is inserted into the patient's vasculature, and moved through the patient's vasculature until the tip of the drainage cannula 12 is disposed in the right atrium. Then, an inlet of the pump 14 is connected to the drainage cannula 12 with inlet connecting tubing 20. Similarly, the pulmonary artery cannula 16 is connected to an outlet of the oxygenator 18 through outlet connecting tubing 22. Another piece of auxiliary connecting tubing 24 is connected between the outlet of the pump 14 and the inlet of the oxygenator 18 to form a circuit. Finally, the pump 14 and the oxygenator 18 secured to the patient. In operation, blood received by the pump 14 from the drainage cannula 12 is pumped to the pulmonary artery through the pulmonary artery cannula 16 to provide right ventricular and respiratory support without having to bypass the heart and lungs.

Holder and Harness

Figure 2:
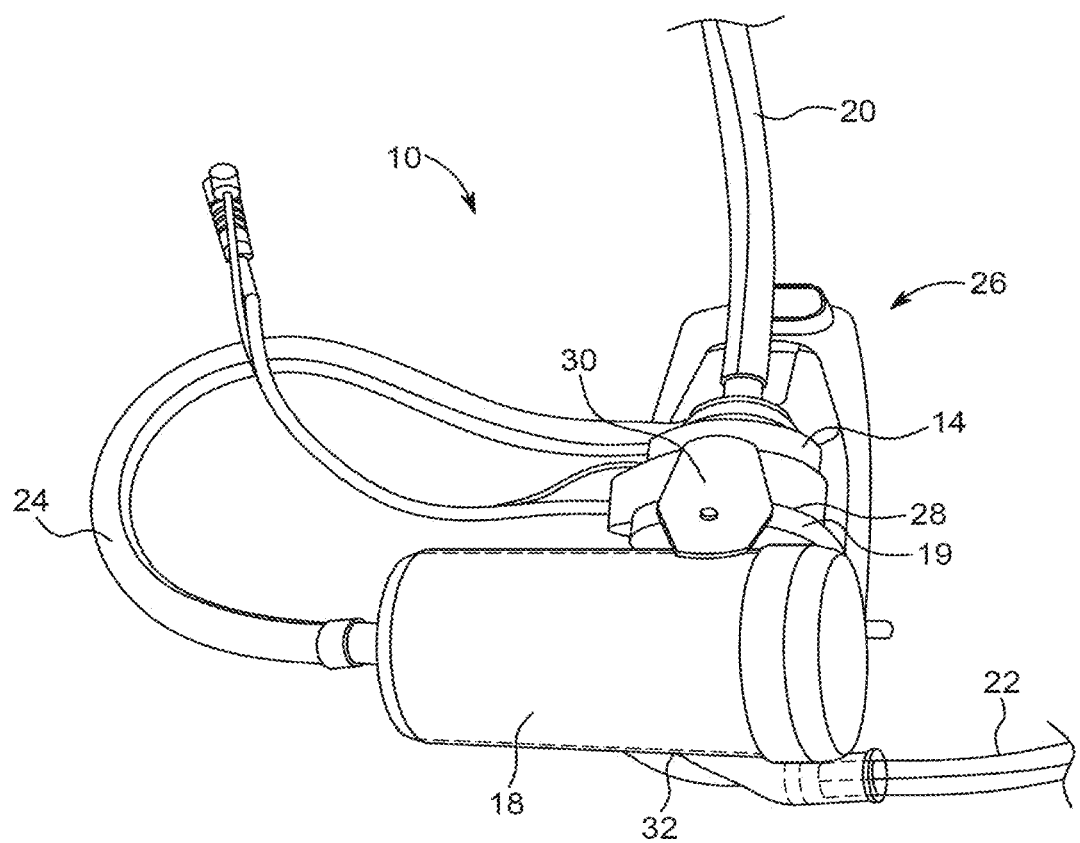
FIG. 2 is a top perspective view of a cardiac assist system including pump, oxygenator, and holder according to an aspect of the disclosure.

Having generally described the cardiac assist system 10, devices for mounting elements of the system 10 together and for securing the system 10 to the patient will now be discussed in detail. With reference to FIG. 2, the system 10 includes a holder 26 which holds the blood pump 14 and oxygenator 18 in place and, in particular, enables a compact connection between the oxygenator 18 and pump 14 in an easily maneuverable package that can be assembled and primed by a single operator. The holder 26 is formed from a suitable rigid material capable of supporting the pump 14 and oxygenator 18 such as high-density polyethylene, polystyrene, or other known biocompatible polymer materials, and can include flexible portions such as tabs, protrusions, or snaps for attaching or connecting the pump 14 and oxygenator 18 to the holder 26. More specifically, the holder 26 includes a pump receiving portion 28 configured to receive the pump 14, which can include a plurality of tabs 30 or snaps for engaging the pump 14 to the holder 26. For example, the pump receiving portion 28 can include a flat surface sized and shaped to receive a base of the pump 14 and one or more tabs 30 extending therefrom for grasping the sides of the pump 14 to hold it in place. The holder 26 also includes an oxygenator receiving portion 32 sized and shaped to receive the cylindrical body of the oxygenator 18. The holder 26 also includes a mechanism, such as a tab or flexible protrusion 19, extending from the holder for connecting the holder 26 to a corresponding structure on the patient such as a connector on a vest, belt, or arm band, as described herein.

One feature of the holder 26 is that by integrating the pump 14 and oxygenator 18, as shown in FIG. 2, priming is simplified by eliminating long connecting tubing and connectors between elements of the system 10. In addition, the pump 14 is positioned and effectively held in place to reduce strain on tubing that can contribute to tubing leaks, kinks in tubing, and similar problems. Further, the shape of the holder 26 is designed to prevent air from entering the patient if an air embolus occurs. Finally, the oxygenator 18 is positioned so that caps and connectors, such as the inlet and outlet of the oxygenator 18, are easily accessible to allow for easy hook-up of tubing and easy removal of condensation build up from the oxygenator 18.

Another feature of the holder 26 is to maintain the position of the pump 14 relative to the cannulae 12, 16 (shown in FIG. 1). In particular, since the cannulae 12, 16 are positioned within the patient's body, it is also desirable to maintain the position of the pump 14 relative to the patient. Mounting the pump 14 to the patient reduces the possibility that the cannulae 12, 16 will be inadvertently pulled out of the patient, or that the cannulae 12, 16 will become disconnected from the pump 14 or the oxygenator 18.

Figure 3:
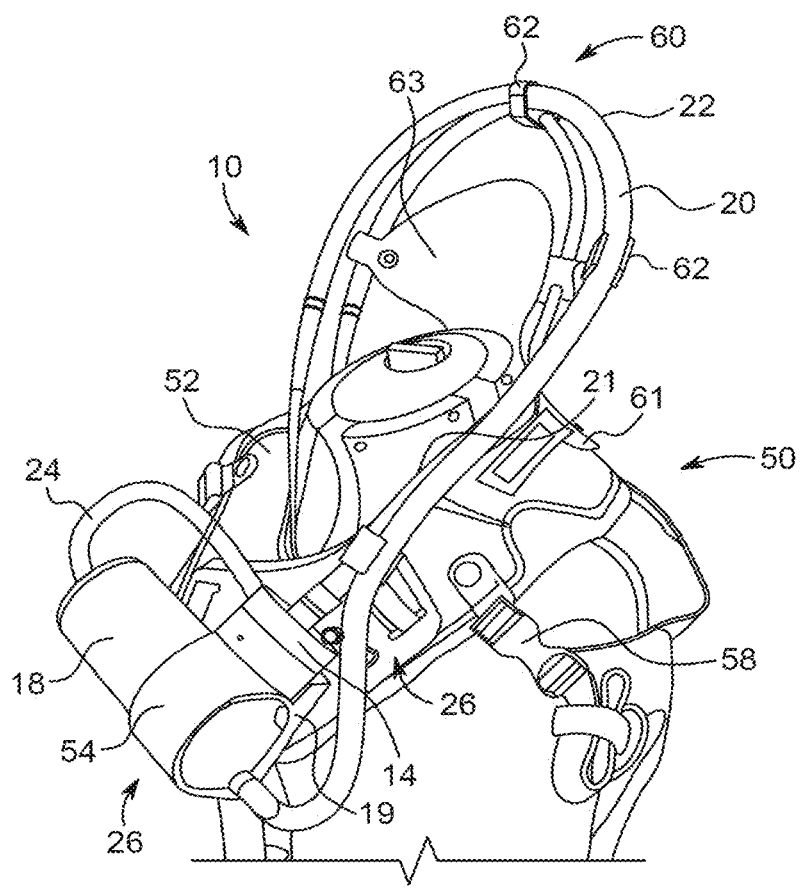
FIG. 3 is a perspective view of a harness for the cardiac assist system of FIG. 2, according to an aspect of the disclosure.
Figure 4:
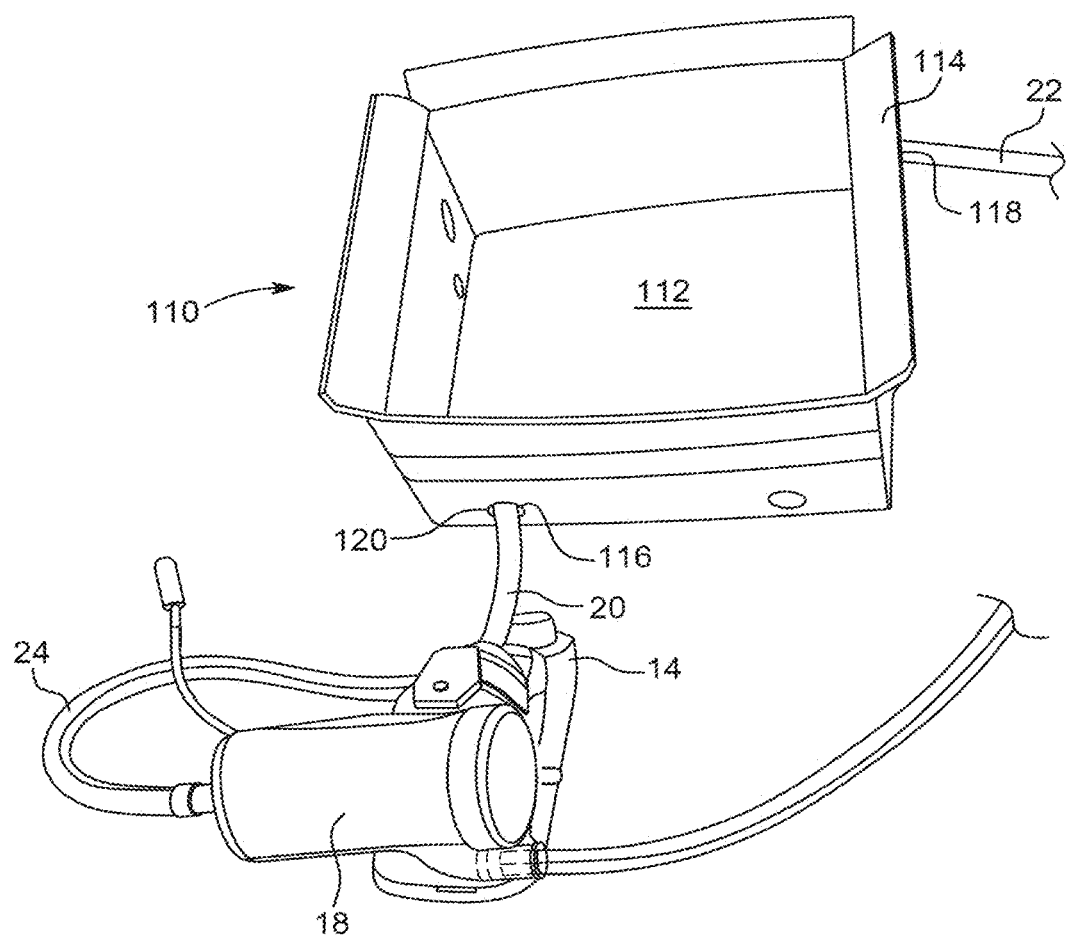
FIG. 4 is a perspective view of a priming tray connected to the cardiac assist system of FIG. 2, according to an aspect of the disclosure.

With reference to FIG. 3, a harness 50 for mounting the system 10, including the pump 14, oxygenator 18, and holder 26, to the patient is illustrated. The harness 50 is configured to mount the elements of the system 10 to the patient in a manner that increases patient mobility, reduces staffing needs, increases safety, and lowers costs. In particular, while wearing the harness 50, the patient is able to walk, lie down, and sit up. The harness 50 includes a vest or sling 52 worn around the upper torso of the patient. In some aspects, the vest or sling 52 is configured to surround the patient's upper torso around the patient's shoulders. The vest or sling 52 may be made from one or more sections that are adjustable in size to better conform to the patient's body. The vest or sling 52 may be formed from a breathable and biocompatible material such as cotton, neoprene, polyester, or nylon. The vest or sling 52 also includes an attachment mechanism 58, such as a fabric hook and loop fastener (e.g., Velcro®) for securing the harness or sling 52 to the patient.

The holder 26, along with the pump 14 and oxygenator 18 attached thereto, are removably mounted to the vest or sling 52. For example, the tab 19 extending from the holder 26 can be configured to be inserted in a slot or receiving portion of the vest or sling 52. Alternatively, or in addition, the vest or sling 52 can include straps 54 that wrap around the holder 26 for attaching the holder 26 to the vest or sling 52. In either case, the holder 26 can be removed from the harness 50 and mounted to a stationary object such as a bedrail, bed, table, or TV pole.

In some aspects, the sling or vest 52 can include a central opening 21 such that the sling or vest 52 can be placed over the head of the patient. The over-the-head design enables placement rapidly of the vest or sling 52 on a patient without having to turn or manipulate the patient's body for implementation. Alternatively, the vest or sling 52 may be wrapped around the upper torso of the patient and can include the attachment mechanism 58, such as a strap and/or a clip, for removably attaching opposing ends of the sling or vest 52 together.

With continued reference to FIG. 3, the connecting tubing 20, 22 is managed with a neck brace 60 and tubing clips 62 for connecting the tubing 20, 22 to the brace 60 and to prevent kinking and dislodgement of the tubing 20, 22. The neck brace 60 has an attachment portion 61 for connecting the neck brace 60 to at least a portion of the vest or sling 52. One or more fastening elements, such as clips, straps, or other mechanical fastening elements, may be provided to secure the attachment portion 61 of the neck brace 60 to the vest or sling 52. A support portion 63 of the neck brace 60 extends from the attachment portion 61 and is configured for supporting at least a portion of the connecting tubing 20, 22. The support portion 63 may extend around at least a portion of a back portion of the user's head. One or more tubing clips 62 are provided on the support portion 63 for receiving the connecting tubing 20, 22. In use, the neck brace 60 enables increased neck mobility compared to other tubing control mechanisms and, in particular, allows the patient to turn his or her head across a full range or a substantial range of motion. While FIG. 3 illustrates the neck brace 60 as a component that is attachable to the vest or sling 52 by an attachment portion 61, the neck brace 60 may be worn separately from the vest or sling 52.

The combination of the harness or sling 52, neck brace 60, and holder 26 allows for a small compact circuit on the patient and, in particular, reduces the length of connective tubing 20, 22 needed for connecting the discharge cannula 12 and pulmonary artery cannula 16 to the patient. As such, a heat exchanger is not required for the system disclosed herein, although a heat exchanger can optionally be used with the system.

Priming the System Prior to Use

An important consideration in connecting and using the system 10 of the present disclosure is to control and, to the extent possible, reduce the priming volume and pressure drop through the tubing 20, 22, 24, the pump 14, and the oxygenator 18. As discussed above in connection with the harness 50 and the holder 26, it is desirable to secure the pump 14 to the patient so that the tubing 20, 22, 24 can be maintained as short as possible, thus minimizing the prime volume, and keeping pressure drop as low as possible. Limiting pressure drop effectively also maximizes the flow rate through the tubing 22, 22, 24. Thus, if one cannula is in the leg and one is in the neck, it is important to provide a means of connecting the two with a circuit as compact as possible. For example, placing the pump 14 adjacent to the upper torso of the patient provides a very short path to one cannula and a longer path to the other cannula. In terms of pressure drops, it is advantageous to minimize the negative pressure drop (very high negative pressure can lead to hemolysis or cavitation in the blood), so it is desirable to locate the pump 14 close to the cannula which takes blood from the patient's right atrium/SVC (Superior Vena Cava)/IVC (Interior Vena Cava) and carries it to the pump 14. The longer tubing run can then be on the outflow side, which is the positive pressure side of the pump 14.

With regard to priming the pump 14 and oxygenator 18, before the pump 14 is attached to the cannula and patient, two chambers (upper and lower) of the pump 14 are primed to prevent air from being pumped into the patient. The lower chamber uses fluid infusate to provide a bearing function to the pump 14 that prevents motor wear, provides cooling, and provides anti-coagulation directly to the upper chamber, where blood flows dining operation of the pump 14. In some aspects, a syringe can be used to push fluid into the lower chamber of the pump 14. The pump 14 is then started, with the pumping action pulling all air through the seal separating the upper and lower chambers. Alternately, a syringe with a two-way stopcock can be used to suck air out of the lower chamber prior to filling the lower chamber with the infusate.

Similarly, the upper chamber, or blood flow chamber, is filled with a priming fluid from either the inflow or outflow port. Owing to the low pump volume, this can be accomplished with saline solution. For example, prior to using the system 10 to treat a patient, the pump 14 and oxygenator 18 are primed by slowly filling the blood chamber of the pump 14 with saline, to remove all air therefrom. Once the air is removed, the tubing 20, 22 can be clamped below the saline line to ensure that a proper wet-to-wet connection is established between the pump 14 inlet and the right atrium cannula 12. The user may also check for air bubbles and, if none are present, can finish pushing tubing 20, 22 over the cannula connector to establish a suitable connection therebetween.

Once a suitable connection between the tubing 20, 22 and cannulae 12, 16 is established, support can be initiated by turning the pump 14 on at low speed, releasing the tubing clamps on the inlet side of the pump 14, and checking for air in the outlet side of the pump 14. If there is no air present, the user releases the remaining tubing clamps, and adjusts the speed until a desired flow rate is achieved.

Priming Tray

Having described the importance of priming the system 10 prior to use, an apparatus for gravity fed priming of the connecting tubing 20, 22 and pump 14 prior to connection to the cannulae 12, 16 will now be discussed in detail. Specifically, with reference to FIGS. 4-7C, a priming tray 110 may be configured to introduce a sterile priming fluid, such as saline, to the pump 14, oxygenator 18, and connecting tubing 20, 22. The priming tray 110 may be configured as a container including an interior reservoir 112 for holding a volume of fluid, such as saline. The container may be constructed from any material suitable for containing the priming fluid. In some aspects, the priming tray 110 may be made from plastic, metal, rubber, and combinations thereof. The priming tray 110 includes an inlet port 114 having an inlet valve connector 118 and an outlet port 116 having an outlet valve connector 120. The inlet and outlet portions 114, 116 extend through a sidewall of the priming tray 110 extending substantially vertically above a bottom surface. The inlet valve connector 118 of the inlet port 114 is configured for connecting the outlet connecting tubing 22 for connection to the oxygenator 18, and the outlet valve connector 120 of the outlet port 116 is configured for connecting to the inlet connecting tubing 20 extending to the inlet port of the pump 14 to form a circuit.

Figure 5A:
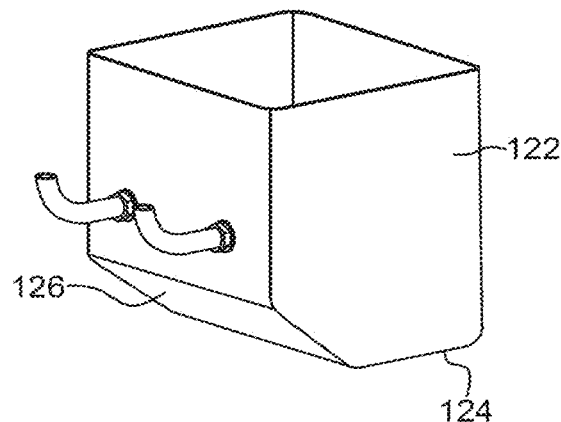
FIG. 5A is a perspective view of another aspect of a priming tray in a standing position.
Figure 5B:
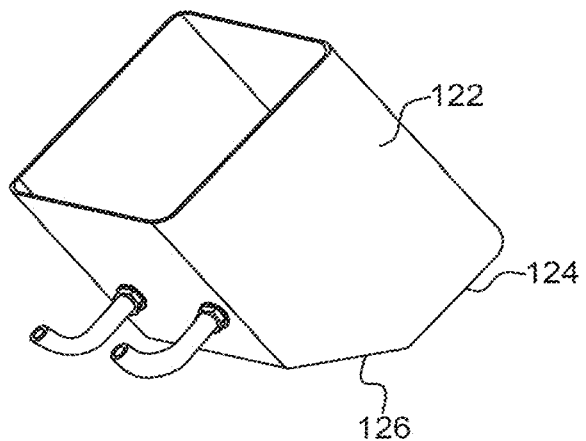
FIG. 5B is a perspective view of the tray of FIG. 5A in a titled position.

The interior reservoir 112 of the priming tray 110 can be tapered or angled towards the outlet port 116 so that the inlet port 114 is at a higher elevation relative to the outlet port 116 when the priming tray 110 is placed on a level surface. In this manner, fluid may be gravity fed from the inlet port 114 to the outlet port 116. In particular, the shape of the interior reservoir 112 of the priming tray 110 is selected to establish quick and accurate priming driven by gravity. The location of the inlet and outlet valve connectors 118, 120 is selected to prevent air lock and to enable gravity priming of the system 10. As shown in FIGS. 5A and 5B, in some aspects, an exterior 122 of the tray 110 includes both a flat base surface 124 and an angled base surface 126. A user can place the tray 110 in an upright position, in which the tray 110 is supported on the flat base surface 124. As shown in FIG. 5B, the tray 110 can also be tilted to rest on the angled surface 126 so that fluid can more easily drain from the inlet port 114 to the outlet port 116. The priming tray 110 enables priming of the pump 14 and/or oxygenator 18 by connecting the inlet and outlet connecting tubing 20, 22 of the system 10 to the inlet and outlet valve connectors 118, 120 and adding a fluid, such as saline, to the reservoir 112 of the priming tray 110. As a result of the shape of the fluid reservoir 112, fluid flows through the outlet connector 120 of the outflow port 116 by gravity.

Figure 6A:
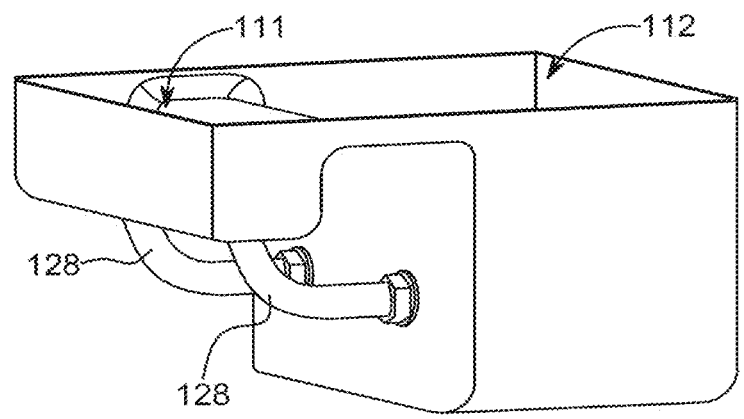
FIG. 6A is a perspective view of another aspect of a priming tray in the standing position.
Figure 6B:
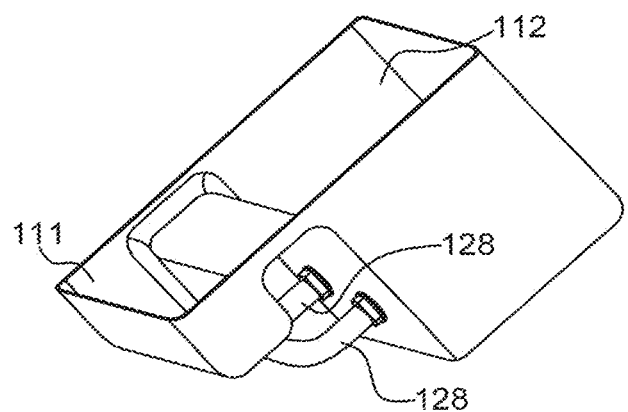
FIG. 6B is a perspective view of the tray of FIG. 6A in the tilted position.

With reference to FIGS. 6A and 6B, the priming tray 110 is illustrated in accordance with another aspect. The priming tray 110 includes an upper interior or reservoir 111 and a lower (main) interior or reservoir 112. The reservoirs 111, 112 are vertically offset relative to one another when the priming tray 110 is placed on a horizontal surface. The reservoirs 111, 112 are connected by tubing 128 extending from a bottom surface of the upper reservoir 111 to a sidewall of the main or lower reservoir 112. In use, fluid introduced to the upper reservoir 111 can flow from the upper reservoir 111 through the tubing 128 and into the lower reservoir 112. Fluid in the lower reservoir 112 can drain through the outlet valve connector 120 and inlet connecting tubing 20 to the pump 14. As in the other aspects described herein, the priming tray 110 can be placed in an angled position, such as shown in FIG. 6B, to increase the fluid flow from the priming tray 110.

Figure 6C:
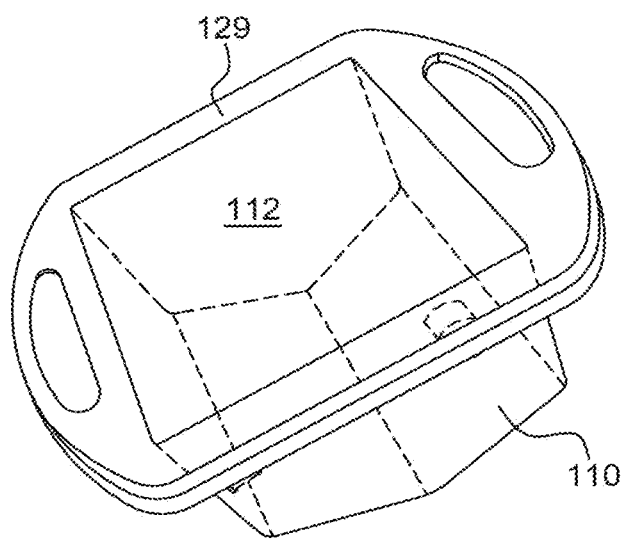
FIG. 6C is a perspective view of another aspect of a priming tray having a lid.

In some aspects, the size of the interior reservoir 112, pump 114, and oxygenator 118 are chosen such that the pump 114, oxygenator 114, and connecting tubing 20, 22, 24 can be placed inside the interior reservoir 112 of the priming tray 110 during shipping. With reference to FIG. 6C, a removable lid 129 may be provided to enclose at least a portion of the interior reservoir 112 during shipping. The lid 129 may further be used during priming to prevent fluid from splashing outside the interior reservoir during priming. The entire package can be sterilized to enable a single operator to prime the system 10 without needing others to assist in the sterilization and/or priming activities as is required in current systems.

Figure 7A:
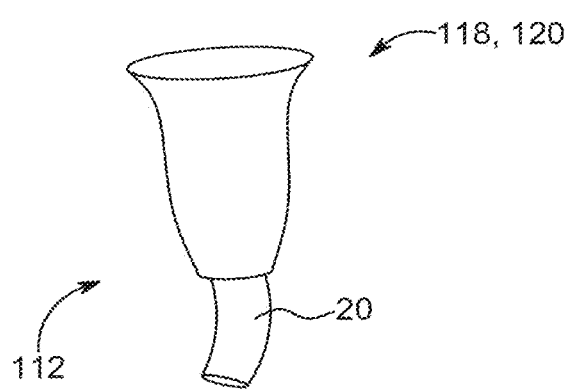
FIG. 7A is a perspective view of an inner portion of the valve connector of the tray of FIG. 4.
Figure 7B:
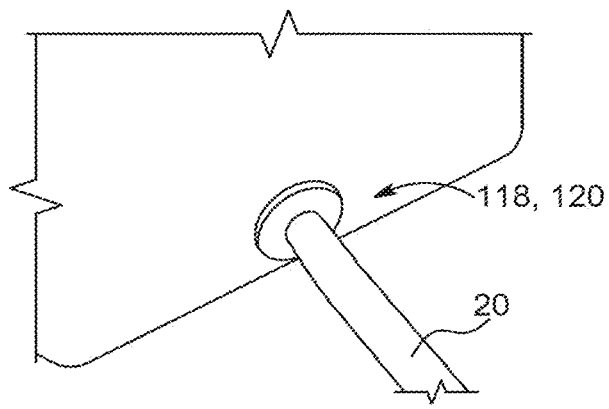
FIG. 7B is a perspective view of the outer portion of the valve connector of the tray of FIG. 4.
Figure 7C:
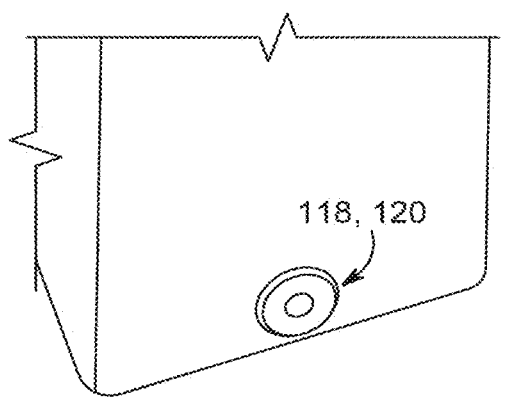
FIG. 7C is a perspective view the outer portion of the valve connector of the tray of FIG. 4 with the connecting tubing removed therefrom.

With specific reference to FIGS. 7A-7C, expanded views of the valve connector 118, 120 between the priming tray 110 and connecting tubing 20, 22 are illustrated. As shown in the figures, the valve connector 118, 120 can include a valve for creating a suitable seal around the flexible tubing to ensure a good connection without leaks. In particular, the shape of the valve connectors 118, 120 is selected to enable priming without spilling fluid during the priming process. More specifically, as shown in FIG. 7A, the connecting tubing 20 is inserted through the valve connector 118 such that the end of the tubing extends into the interior 112 of the priming tray 110. The valve seals around the sidewall of the connecting tubing 20, 22 to prevent leaks. The valve connector 118, 120 is also configured to automatically reseal when the tubing 20, 22 is removed from the connector 118, 120 to prevent spillage. In use, once the system 10 is primed, the connecting tubing 20, 22 is removed from the tray 110 and connected to the drainage or pulmonary artery cannulae 12, 16 so that cardiac assistance to the patient can be provided.

Wet-to-Wet Connector

Having described the cardiac assist system 10 and priming tray 110 for priming the pump 14 and oxygenator 18, connector 200 for connecting the primed connecting tubing 20, 22 to the cannulae 12, 16 will now be discussed in detail. As with the process for priming the pump 14 and oxygenator 18, it is important to remove air from the connector 200 and connecting tubing 20, 22 prior to connection to the cannulae 12, 16 to form a secure connection.

Figure 8A:
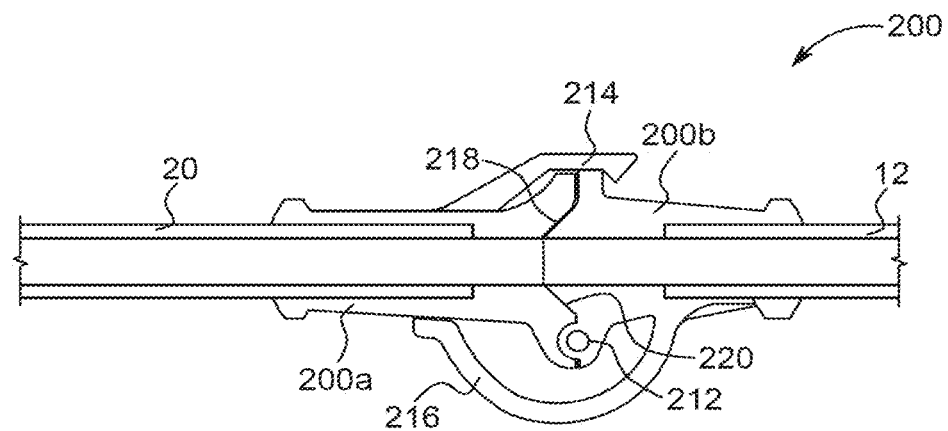
FIG. 8A is a schematic drawing of a quick release wet-to-wet connector for introducing saline to a fluid line in a closed position, according to an aspect of the disclosure.
Figure 8B:
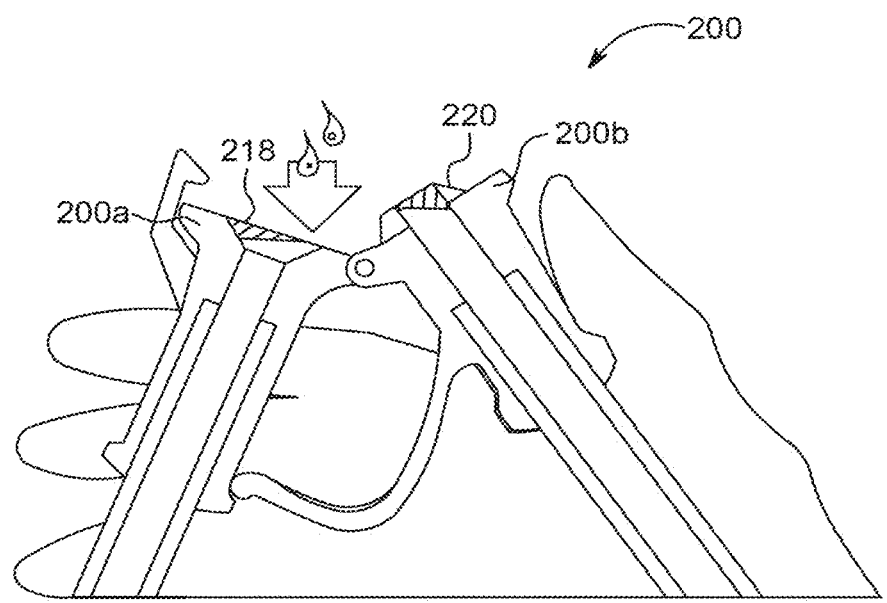
FIG. 8B is a schematic drawing of the quick release connector of FIG. 8A in an open position.

With reference to FIGS. 8A and 8B, the connector 200 is an automatically closing joint including a hinge 212 and lock mechanism or latch 214 for connecting two ends of a fluid conduit, such as an end of connecting tubing 20 and a proximal end of a catheter or cannula 12. While FIGS. 8A-8B illustrate the connector 200 for connecting the inlet connecting tubing 20 with the drainage cannula 12, it is to be understood that the same connector 200 can be used for connecting the outlet connecting tubing 22 with the femoral or pulmonary artery cannula 16. The connector 200 includes a first portion 200a connected to the first tubing portion, such as the inlet connecting tubing 20, and a second portion 200b connected to the second tubing portion, such as the femoral or pulmonary artery cannula 16. The first and second portions 200a, 200b are hingedly coupled together by the hinge 212. The hinge 212 and/or one of the first and second portions 200a, 200b can include a biasing member, such as a spring 216, that automatically closes to connect the ends of the opposing first and second portions 200a, 200b together when the user releases one of the first portion 200a or the second portion 200b. In particular, as shown in FIGS. 8A and 8B, the connector 200 is transitionable from an open position, in which the ends of the connecting tubing 20 and the cannula 12 are disconnected from one another, to a closed position in which the ends of the connecting tubing 20 and the cannula 12 are connected together to enable fluid to pass therebetween through the connector 200. Initially, with the connector 200 in the open position, the user can introduce saline to the connecting tubing 20 and the cannula 12 for priming the connector 200. Once the fluid conduits are filled, as shown in FIG. 8B, the user can transition the connector 200 back to the closed position, such as by releasing one of the first portion 200a or the second portion 200b and allowing the biasing member to bias the connector 200 to a closed position. Once the connector 200 is filled and in the closed position, fluid communication can be established from the patient to the pump 14 through the connector 200 and connecting tubing 20.

The connector 200 can be a one-handed connector that can be grasped by a user with one hand and held in an open position with one hand. When the user releases the connector 200, the spring 216 exerts a biasing force which returns the connector 200 to the closed position. It is noted that the ends of the fluid conduits that are connected together through the connector 200 may be shaped such that one end is inserted in the end of the other fluid connector. For example, the end of one of the first portion or the second portion 200a, 200b can include an outwardly flared portion 218 that is sized to receive a corresponding tapered portion 220 of the other of the first portion 200a and the second portion 200b, as shown in FIGS. 8A and 8B.

Figure 9A:
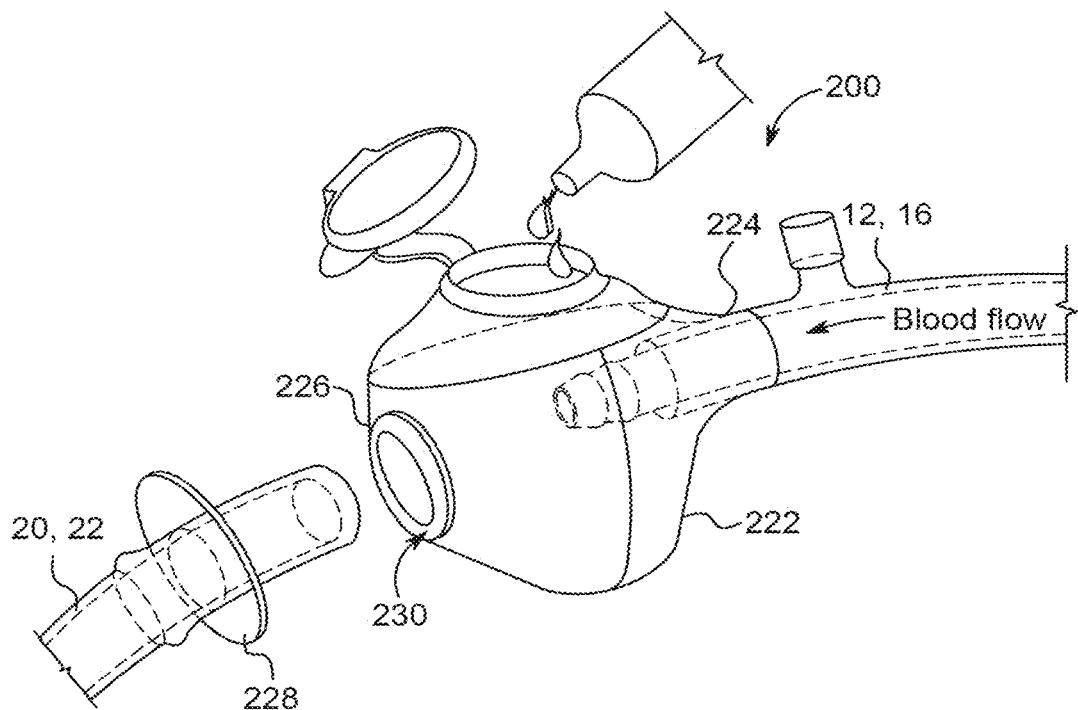
FIGS. 9A and 9B are schematic drawings of a submersed component connector for forming a wet-to-wet connection between portions of tubing, according to another aspect of the disclosure.
Figure 9B:
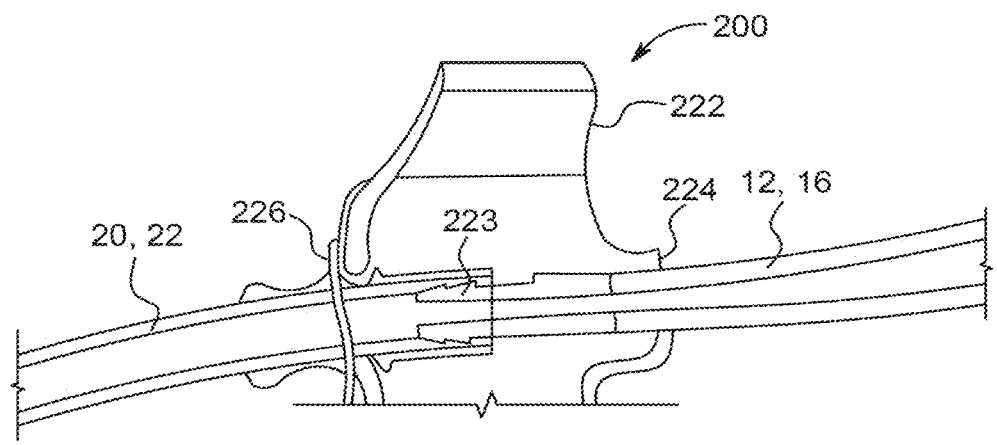

With reference to FIGS. 9A and 9B, in another aspect, the connector 200 includes a submersible component having a housing or enclosure 222, with opposing ports for receiving ends of fluid conduits. In some aspects, the housing or enclosure 222 may be formed as a flexible bag. A port 224 located on an end of the housing or enclosure 222 can be connected to a proximal end of the cannulae 12, 16. In some aspects, the cannulae 12, 16 can be non-removably coupled with the housing or enclosure 222. A port 226 located on the opposing end of the housing or enclosure 222 can be configured to removably receive the end of the connecting tubing 20, 22 extending from the pump 14 or oxygenator 18. As shown in FIG. 9B, the end of the cannulae 12, 16 can have a tapered nozzle or connector 223, such as a luer connecter, for establishing a fluid connection between the cannulae 12, 16 and tubing 20, 22. Other connectors, such as threaded connectors, snap fit connectors, and the like can also be used. The end of the connecting tubing 20, 22 is inserted through the port 226 and into the interior of the housing or enclosure 222 for removably connecting with the connector 223 of the cannulae 12, 16. In some embodiments, the connecting tubing 20, 22 can include a radially extending flange 228 configured to cover the port 226 to form a suitable seal between the connecting tubing 20, 22 and port 226. The port 226 can also include an annular rubber wiper 230 for sealing the port 226 to prevent spillage when the connecting tubing 20, 22 is removed from the port 226. In use, the end of the connecting tubing 20, 22 is inserted into the port 226 to form a seal, but is not connected to the cannulae 12, 16. The interior of the bag 222 is then filled with saline to prime or remove air from the connector 200 and connecting tubing 20, 22. Once the bag 222 is filled with a sufficient volume of fluid, the end of the connecting tubing 20, 22 can be pushed toward the end of the cannulae 12, 16 to form a suitable connection therebetween.

Figure 10:
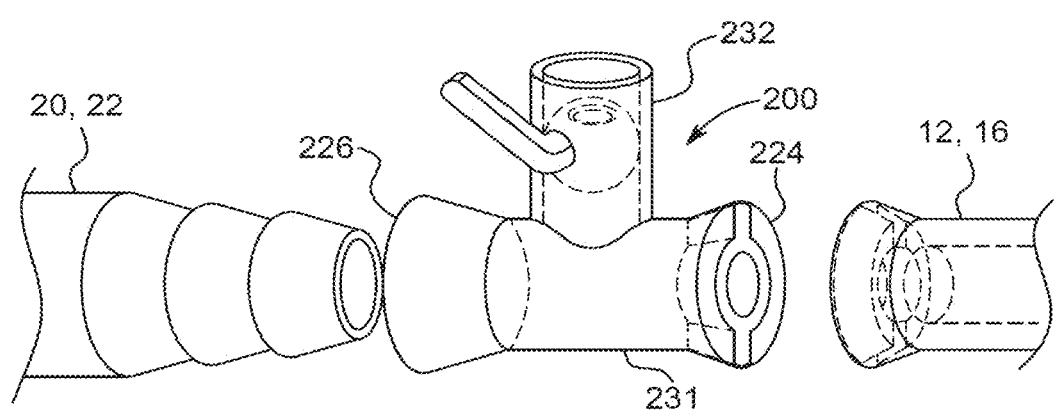
FIG. 10 is a schematic drawing of another aspect of a wet-to-wet tubing connector, according to an aspect of the disclosure.

With reference to FIG. 10, in another embodiment, the connector 200 includes a tubular housing 231 shaped like a three-way valve or T-connector. The housing 231 includes a first end or port 224 for receiving a cannulae 12, 16 and a second end or port 226 sized and shaped to connect with connecting tubing 20, 22 extending from the pump 14 or oxygenator 18. The cannula receiving end or port 224 can be fused to the cannulae 12, 16 or removably attached thereto. The connecting tubing receiving end or port 226 can include a tapered opening configured to engage a male luer connector of the connecting tubing 20, 22. Other connectors, such as threaded connectors, snap fit connectors, and the like can also be used. A fluid entry port 232 extends from a central portion of the connector housing 231. The fluid entry port 232 can include a valve, such as a ball valve 234, for selectively opening or closing the fluid entry port 232 to allow air or fluid to pass therethrough. In use, once the connecting tubing 20, 22 and cannulae 12, 16 are connected to the housing 231, the ball valve 234 is opened and fluid is introduced through the valve 234. Once a suitable amount of fluid to effectively remove air from the system 10 is added, the valve 234 can be closed to establish a suitable connection between the connectors 200 and cannulae 12, 16.

Figure 11A:
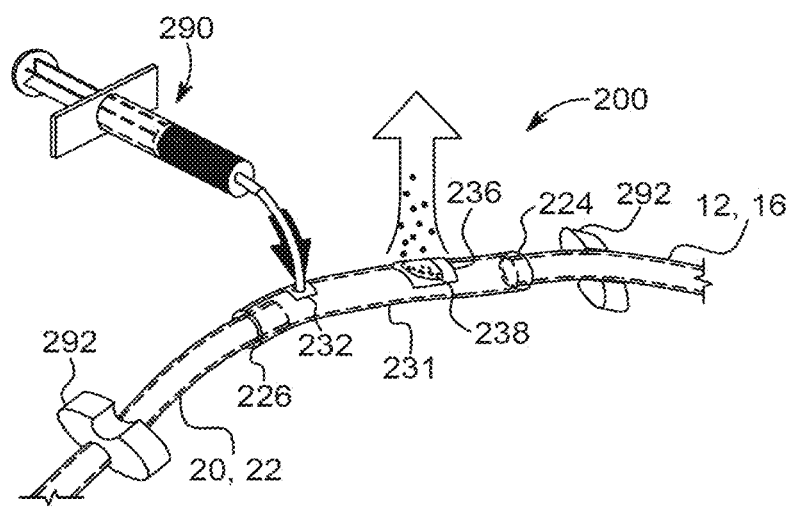
FIGS. 11A and 11B are schematic drawings of a tubing connector including a integral hydrophobic membrane, according to an aspect of the disclosure.
Figure 11B:
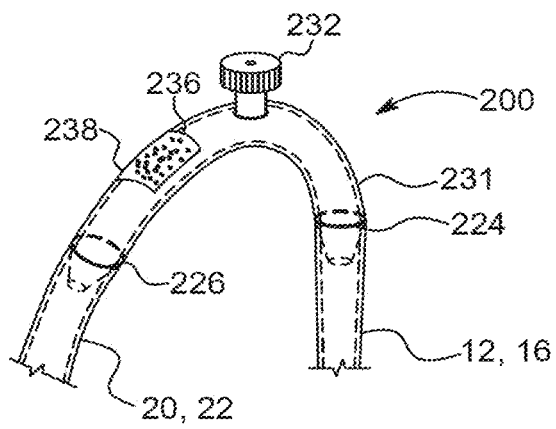

With reference to FIGS. 11A and 11B, another embodiment or aspect of a connector 200 for introducing fluid into the system 10 using a syringe 290 is illustrated. As in previously described embodiments or aspects, the connector 200 includes an elongate tubular housing 231 including a first port 224 for connection to a cannulae 12, 16 and an opposing second port 226 for connection to connecting tubing 20, 22 extending from the pump 14 or oxygenator 18. The elongate tubular housing 231 includes a side port or fluid entry port 232 extending from a sidewall thereof and connected to the syringe 290 for introducing a priming fluid, such as saline, to the connector 200. The sidewall of the elongate tubular housing 231 also includes a second opening 236 covered by a hydrophobic membrane 238. When saline is expelled from the syringe 290 and introduced to the connector 200, any trapped air is permitted to escape from the elongate tubular housing 231 through the hydrophobic membrane 238. Once all air is expelled from the connector, the clamps 292 can be released for permitting fluid flow from the connecting tubing 20,22, through the connector 200, and to the cannulae 12, 16.

Figure 12A:
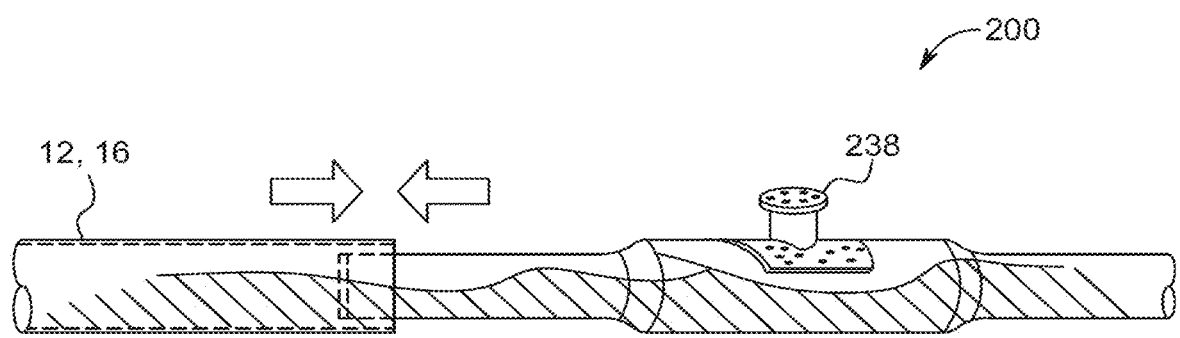
FIGS. 12A and 12B are schematic drawings of another embodiment of a tubing connector with an overlapping tubing design, according to an aspect of the disclosure.
Figure 12B:
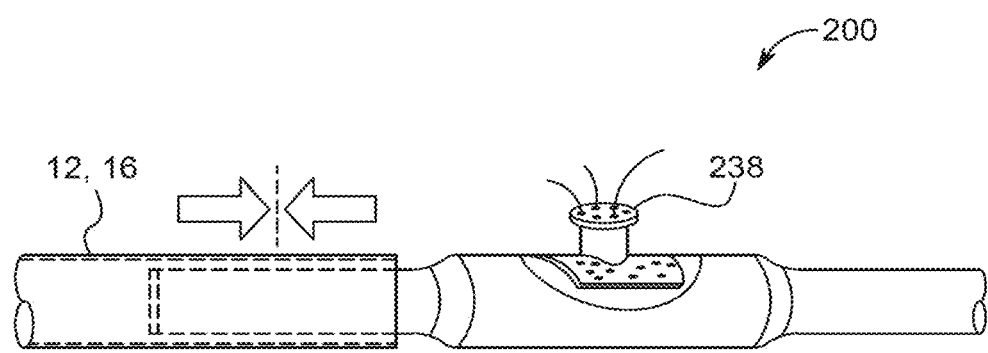

With reference to FIGS. 12A and 12B, in another embodiment, the connector 200 includes an overlapping tube design for pressing an enlarged proximal end of the cannulae 12, 16 or connecting tubing 20, 22 over a corresponding portion of the connector 200. As the cannulae 12, 16 and connector 200 are brought together, the volume of the interior of the connector 200 is reduced causing any air in the interior of the connector 200 to be forced out of the connector 200 through a port covered by the hydrophobic membrane 238.

Figure 13A:
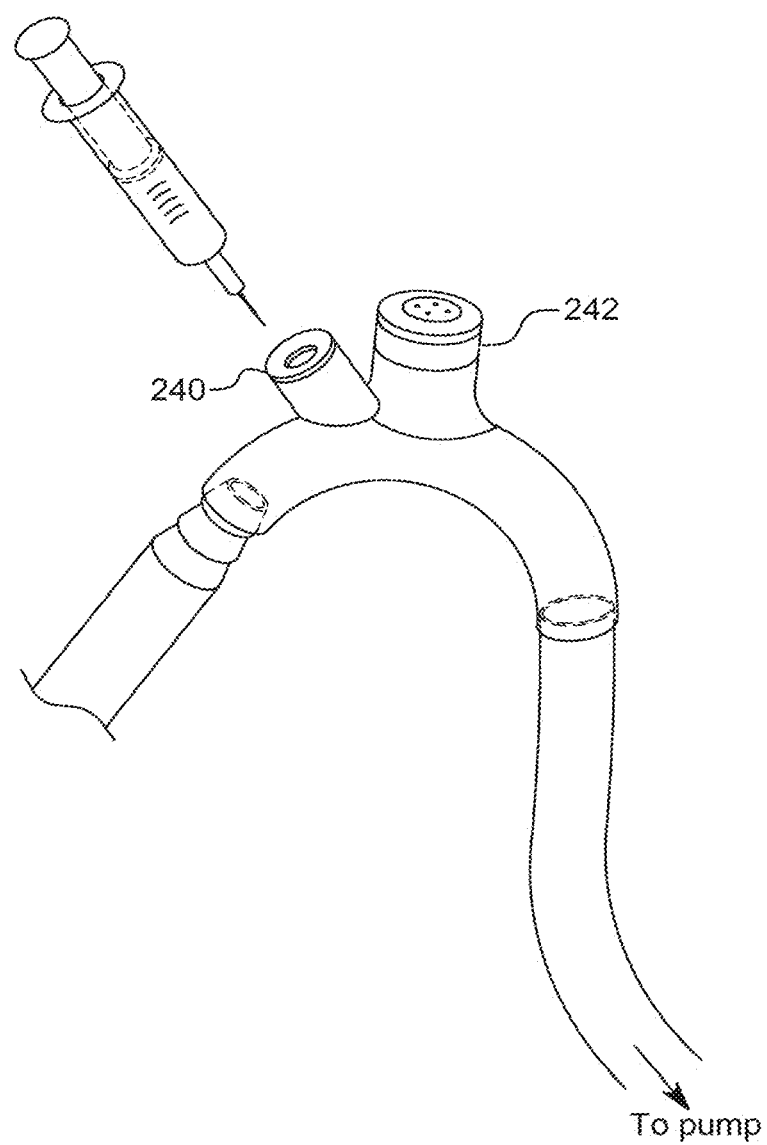
FIG. 13A is a schematic drawing of another embodiment of a tubing connector according to an aspect of the disclosure.

With reference to FIG. 13A, in another embodiment, the connector 200 and system 10 are configured to allow a user to draw air from the connector 200 using a syringe 290. As in previously described embodiments, the connector 200 includes an elongate tubular housing 231 having a first port 224 and a second port 226 for connection with the cannulae 12, 16 and connecting tubing 20, 22, respectively. The connector 200 also includes a resealable port 240 covered by a piercable septum configured to be pierced by the syringe 290 and a separate port with a one-way valve 242 for allowing air to escape from an interior of the connector housing 231. In use, the user inserts a full syringe 290 containing a priming fluid, such as saline, through the piercable septum. The user expels the fluid from the syringe 290 and into the housing 231. After the housing 231 is filled, the filled connector 202 is connected to flexible connecting tubing 20, 22 extending to the pump 14 or oxygenator 18. Any air that is trapped in the connector 200 as fluid is being expelled into the housing 231 can escape through the port covered by the one-way valve 242.

Figure 13B:
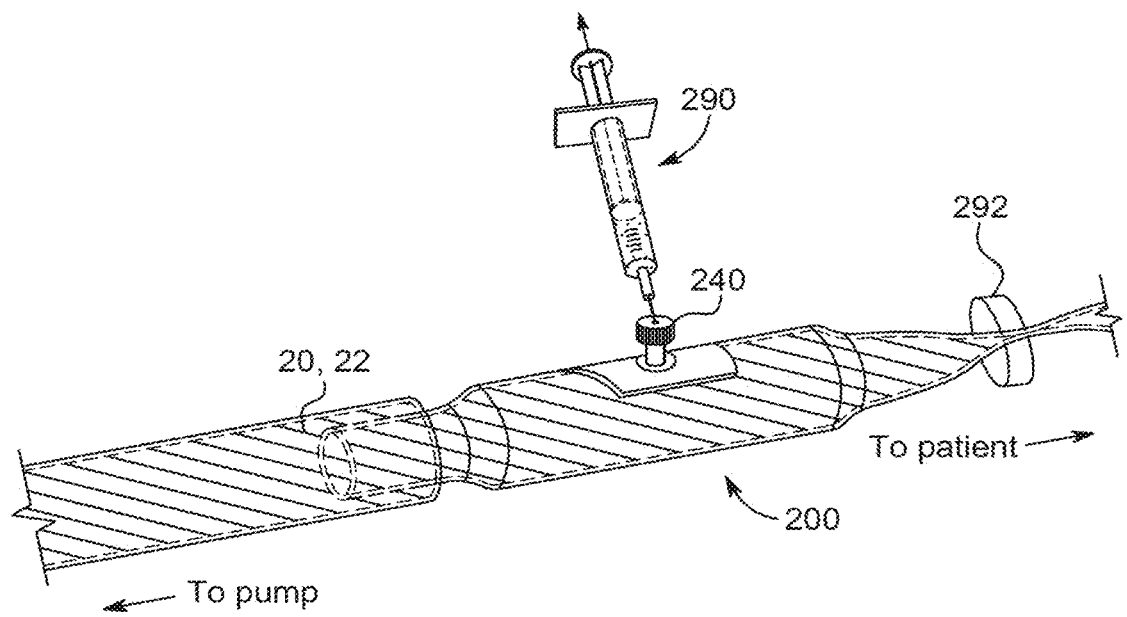
FIG. 13B is a schematic drawing of another embodiment of a tubing connector, according to an aspect of the disclosure.

Alternatively, as shown in FIG. 13B, after the fluid is injected into the housing 231, the user can insert an empty syringe 290 through the piercable septum and remove any trapped air from the interior of the housing 231 by drawing the plunger of the syringe 290 in a proximal direction through the syringe barrel. Once all air is removed, a clamp 292 on the cannula can be removed to establish fluid communication between the pump 14 or oxygenator 18 and the patient through the connector 200 and cannulae 12, 16.

Figure 14A:
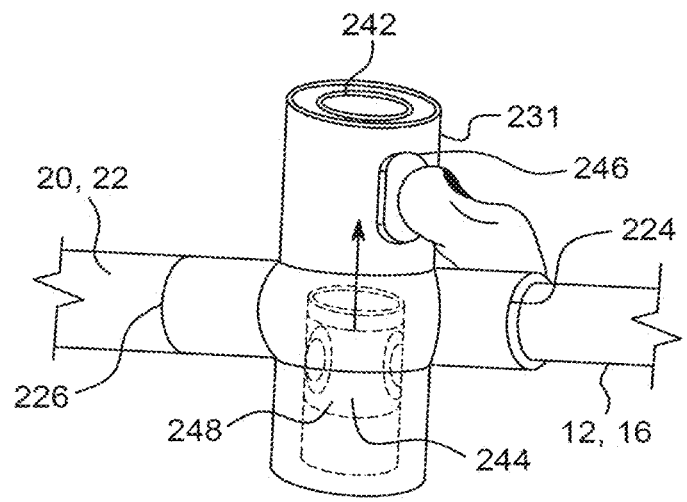
FIGS. 14A and 14B are schematic drawings of an embodiment of a tubing connector including an automated saline fill mechanism, according to an aspect of the disclosure.
Figure 14B:
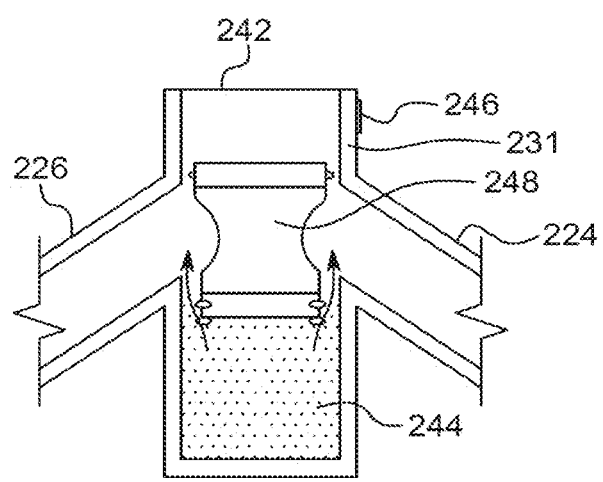

With reference to FIGS. 14A and 14B, an automated saline fill connector 200 is illustrated. As in previously described embodiments, the connector 200 includes a housing 231 with a first port 224 for connection to a cannulae 12, 16 and a second port 226 for connection to flexible connecting tubing 20, 22 leading to the pump 14 or oxygenator 18. The housing 231 encloses a prefilled saline pressurized micro-canister 244. The micro-canister 244 is controlled by a release button 246 extending through the housing 231. As shown in FIG. 14B, the canister 244 includes a movable cap or piston 248 extending from the top of the canister 244. When the canister 244 is activated by pressing the release button 246, the cap or piston 248 is moved in an upward direction pushing air away from the interior of the connector 230 and toward a one-way valve 242. Once the cap or piston 248 is released, pressurized saline is permitted to flow from the canister 244, through the interior of the housing 231, and towards the connecting tubing 20, 22 and cannulae 12, 16. As in previously described connectors, once the tubing 20, 22 and pump are primed, a clamp 292 on the cannulae 12, 16 can be opened for establishing fluid communication between the pump 14 and the patient.

While specific embodiments and aspects have been described in detail in the foregoing, it will be appreciated by those skilled in the art that various modifications and alternatives to those details could be developed in light of the overall teachings of the disclosure. Accordingly, the particular arrangements disclosed are meant to be illustrative only and not limiting as to the scope of invention. Further, although the invention has been described in detail for the purpose of illustration based on what is currently considered to be the most practical and preferred embodiments and aspects, it is to be understood that such detail is solely for that purpose and that the invention is not limited to the disclosed embodiments and aspects, but, on the contrary, is intended to cover modifications and equivalent arrangements that are within the spirit and scope of the appended claims. For example, it is to be understood that the present invention contemplates that, to the extent possible, one or more features of any embodiment or aspect can be combined with one or more features of any other embodiment or aspect.

What is claimed is:

1. A method for priming a cardiac assist system, the method comprising:
    connecting tubing of a first component of the cardiac assist system to an inlet port of a priming tray;
    connecting tubing of a second component of the cardiac assist system to an outlet port of the priming tray;
    the priming tray comprising:
        a body having a base wall and a plurality of side walls upstanding from the base wall to define an interior reservoir configured for holding a volume of fluid, the base wall defining a first planar base surface and a second planar base surface extending on an obtuse angle from the first planar base surface;
    filling the interior reservoir with the fluid while the priming tray is in a first position in which the body is supported on the first planar base surface;
    tilting the priming tray from the first position to a second position where the body is tilted to rest on the second planar base surface;
    wherein when the body is tilted from the first position to the second position, the fluid flows through the tubing of the first component and the tubing of the second component to prime the cardiac assist system with the fluid from the priming tray via gravity.

2. The method of claim 1, wherein the inlet port is at a higher position relative to the outlet port when the body is in the second position.

3. The method of claim 1, wherein connecting the tubing of the first component of the cardiac assist system to the inlet port of the priming tray includes inserting the tubing of the first component of the cardiac assist system through the inlet port into the interior reservoir.

4. The method of claim 3, wherein connecting the tubing of the second component of the cardiac assist system to the outlet port of the priming tray incudes inserting the tubing of the second component of the cardiac assist system through the outlet port into the interior reservoir.

5. The method of claim 4, wherein the inlet port comprises a seal configured to prevent leakage of the fluid around the tubing of the first component of the cardiac assist system.

6. The method of claim 5, wherein the outlet port comprises a seal configured to prevent leakage of the fluid around the tubing of the second component of the cardiac assist system.

7. The method of claim 1, wherein the inlet port of the priming tray is on a first one of the plurality of side walls, and the outlet port of the priming tray is on the first one of the plurality of side walls or a second one of the plurality of side walls.

8. The method of claim 1, further comprising tilting the priming tray back from the second position to the first position.

9. The method of claim 1, further comprising enclosing the interior reservoir of the priming tray with a removable lid.

10. The method of claim 1, wherein the interior reservoir of the priming tray is angled or tapered toward the outlet port when the priming tray is resting on the second planar base surface.

\* \* \* \* \*